United States Patent [19]
Giani et al.

[11] Patent Number: 5,747,004
[45] Date of Patent: May 5, 1998

[54] SELF-HEATING DENTIFRICE

[75] Inventors: Paola Giani, Perchiera Borromeo; Massimo L'Abbate, Polignano a Mare, both of Italy; Lewis Patrick Cancro, Trumbull, Conn.

[73] Assignee: Chesebrough-Pond's USA Co., Division of Conopco, Inc., Greenwich, Conn.

[21] Appl. No.: 676,613

[22] Filed: Jul. 10, 1996

[30] Foreign Application Priority Data

Jul. 10, 1995 [EP] European Pat. Off. .............. 95201882

[51] Int. Cl.$^6$ .............................. A61K 7/16; A61K 7/18; A61K 7/20
[52] U.S. Cl. ................... 424/49; 424/52; 424/53; 424/57
[58] Field of Search ........................... 424/49–58

[56] References Cited

U.S. PATENT DOCUMENTS

| | | |
|---|---|---|
| 3,574,824 | 4/1971 | Echeandia et al. ............ 424/50 |
| 4,115,293 | 9/1978 | Schoenholz et al. ............ 252/102 |
| 4,132,771 | 1/1979 | Schreiber et al. . |
| 4,159,316 | 6/1979 | Januszewski et al. . |
| 4,187,287 | 2/1980 | Schrieber et al. ............ 424/49 |
| 4,626,550 | 12/1986 | Hertzenberg ............ 424/49 |
| 4,647,451 | 3/1987 | Piechota ............ 424/52 |
| 4,891,211 | 1/1990 | Winston, II ............ 424/52 |
| 4,913,168 | 4/1990 | Potter et al. ............ 131/194 |

FOREIGN PATENT DOCUMENTS

| | | |
|---|---|---|
| 0 187 912 | 7/1986 | European Pat. Off. . |
| 359071 | 9/1922 | Germany . |
| 57/99514 | 11/1980 | Japan . |
| 62/30704 | 1/1985 | Japan . |
| 2 220 141 | 1/1990 | United Kingdom . |

*Primary Examiner*—Shep K. Rose
*Attorney, Agent, or Firm*—Milton L. Honig

[57] ABSTRACT

The present invention relates to a dentifrice that is capable of generating heat upon use in the oral cavity. The dentifrice contains an effective amount of a heat of hydration generating hydratable inorganic or organic salt. A preferred salt is anhydrous sodium carbonate.

5 Claims, No Drawings

SELF-HEATING DENTIFRICE

The present invention relates to a self-heating dentifrice, that is a dentifrice composition which, when used in the oral cavity, is capable of generating heat in the oral cavity.

Self-heating dentifrices are already known in the art. Thus, in U.S. Pat. No. 4,159,316 (Januszewski et al.) and in U.S. Pat. No. 4,132,771 (Schreiber et al.) self-heating dentifrices are described which are anhydrous compositions that contain, as heat-generating component, an anhydrous synthetic zeolite which is also the sole or major abrasive cleaning agent in the dentifrice composition. Up to 20% by weight of additional abrasive cleaning agents can be included in the compositions of these prior proposals.

The use of special types of zeolites in self-warming personal care products such as creams, lotions is described in EP-A-0,187,912 (PQ Corp.).

From DE-C-359,071 (Bilke) it is known to add a heat-generating substance like magnesiumchloride to a mouthwash just prior to using the mouthwash for rinsing the mouth.

In JP-A-05/229920 (Murai) a hair tonic rinse agent in powder form is described, which contains powdered carbonates. This rinse agent is stated to generate heat.

Similarly, in JP-A-57/099514 (Jiyonson) heat-generating hair care products are described which contain heat-generating substances like calcium- and magnesium chloride, zinc sulphate and dried alum.

In JP-A-62/030704 (Kobayashi KOVC K.K.) a heat-generating pack cosmetic is described, which contains calcined gypsum as heat-generating substance.

None of these references are concerned with an anhydrous self-heating dentifrice.

We have now found that self-heating dentifrices can also be prepared without having to use synthetic zeolites as the sole or major abrasive cleaning agent, by using in an anhydrous vehicle a hydratable, inorganic or organic salt that generates heat of hydration when water is added thereto, e.g. upon normal use of the dentifrice in the oral cavity. Upon such use, the hydratable salt is hydrated, releasing heat of hydration which produces an increase in temperature of the dentifrice in the oral cavity.

The present invention, therefore, relates to an anhydrous, self-heating dentifrice which is substantially free from anhydrous synthetic zeolites, and is characterised in that it contains an effective amount of a heat of hydration generating, hydratable, inorganic or organic salt.

The hydratable inorganic or organic salt should be hydratable, i.e. should be capable of taking up water in the form of water of crystallisation. The salt may be partially hydrated, or it may be anhydrous. Anhydrous hydratable salts are preferred. The salt should, of course, be pharmaceutically and cosmetically acceptable for inclusion in a dentifrice, and the choice of a suitable salt is also governed by the degree of self-heating that is required in the dentifrice of the present invention.

In general, the degree of self-heating should be such that upon normal use of the dentifrice when brushing one's teeth the temperature of the dentifrice/saliva mixture in the oral cavity reaches after 30 seconds a value of 25° C. or higher and after 1 minute a value of 29° C. or higher.

Preferably, the difference between the initial temperature and the increased temperature should be no more than 15° C., and should preferably between 3° and 10° C. after 2 minutes. Best results are obtained with a Δt of between 5° and 7° C. after two minutes.

Too high a temperature, e.g. of 40° C. or above should be avoided, as this may cause an unpleasant sensation in the oral cavity. By the choice of the hydratable salt and the amount thereof, the degree of self-heating in the oral cavity can be controlled. In general, the amount of the hydratable salt will range between 2 and 25% by weight, usually between 3 and 20% by weight and preferably between 5 and 15% by weight of the composition. It is to be noted that if the dentifrice contains optional ingredients which upon hydration or solution absorb heat, the amount of the heat-generating hydratable salt required will be at the higher end of these ranges to compensate for this heat absorbed and to still provide the self-heating effect.

Suitable examples of inorganic or organic hydratable salts are (in partially hydrated form or in anhydrous form) alkalimetal orthophosphates, alkalimetal pyrophosphates, alkalimetal carbonates, alkalimetal sesquicarbonates, alkalimetal borates, calcium chloride, magnesium chloride, calciumsulphate, alkalimetal acetates, alkalimetal citrates, alkalimetal phosphonates, zinc citrate, zinc sulphate, zinc nitrate, etc.. As said before, the dentifrice of the invention is substantially free from anhydrous synthetic zeolites, as these when used together with the hydratable salt of the invention would produce too high a temperature increase. Preferred are anhydrous salts, and particularly preferred is anhydrous sodium carbonate. Mixtures of various, partially hydrated and/or anhydrous salts may also be used. For the preferred anhydrous sodium carbonate the amount, present in the composition of the invention, generally ranges from 5–20% by weight, preferably from 6–15% by weight.

The balance of the dentifrice of the invention consists of an anhydrous liquid vehicle and optional, conventional dentifrice ingredients. The final dentifrice composition must be substantially anhydrous, which means that it may not contain more than 3% free water, which limit is inclusive of any free water, present in the ingredients of the dentifrice. Preferably, the composition does not contain more than 1% free water, and is particularly preferably fully anhydrous.

Thus, the dentifrices of the present invention contain optional further ingredients such as pharmaceutically acceptable carriers like starch, sucrose, alcohol systems etc. Small amounts of surfactants may also be included, such as anionic, nonionic and amphoteric surfactants. They may further contain all the usual dentifrice ingredients. Thus, they may comprise particulate abrasive materials including agglomerated particulate abrasive materials such as silicas, aluminas, calcium carbonates (both natural and synthetic), dicalciumphosphates, calcium pyrophosphates, hydroxyapatites, trimetaphosphates, insoluble hexametaphosphates and so on, usually in amounts between 5 and 60% by weight.

Furthermore, the dentifrice formulations may comprise humectants such as glycerol, sorbitol, polyethyleneglycol, propyleneglycol, xylitol, lactitol and so on. Humectant systems comprising glycerol or propyleneglycol as the major constituent (>30%) are preferred for paste-consistency reasons.

Binders and thickeners such as sodium carboxymethylcellulose, xanthan gum, gum arabic etc. may also be included, as well as synthetic polymers such as polyacrylates and carboxyvinyl polymers such as Carbopol®.

Flavours such as peppermint and spearmint oils may also be included, as well as preservatives, opacifying agents, colouring agents, pH-adjusting agents, sweetening agents and so on.

Anti-bacterial agents may also be included such as copper-, zinc- and stannous salts such as zinc citrate, sodium zinc citrate and stannous pyrophosphate, sanguinarine extract, thymol, eugenol, methyl salicylate, metronidazole. Further examples of anti-bacterial agents are quaternary ammonium compounds such as cetylpyridinium chloride; bis-biguanides such as chlorexidine, chlorhexidine digluconate, hexetidine, octenidine, alexidine; Triclosan and other halogenated bisphenolic compounds such as 2,2' methylenebis-(4-chloro-6-bromophenol).

Polymeric compounds which can enhance the delivery of active ingredients such as anti-bacterial agents can also be included. Examples of such polymers are copolymers of polyvinylmethylether with maleic anhydride and other similar delivery enhancing polymers, e.g. those described in DE-A-3,942,643 (Colgate)

Furthermore anti-inflammatory agents such as ibuprofen, flurbiprofen, aspirin, indomethacin etc. may also be included.

Anti-caries agents such as sodium- and stannous fluoride, aminefluorides, monosodiumfluorophosphate, casein, plaque buffers such as urea, pyruvates, arginine, small peptides, calcium glycerophosphate, strontium polyacrylates may also be included. Other optional ingredients include vitamins such as Vitamin C, and plant extracts. Desensitising agents such as potassium tartrate, potassium citrate, potassium chloride, potassium bicarbonate, potassium oxalate, potassium nitrate, calcium phosphates as well as strontium salts may also be included.

Furthermore, the oral compositions may comprise anticalculus agents such as alkalimetal pyrophosphates, hypophosphite-containing polymers, organic phosphonates, phosphocitrates etc.

In addition, the compositions may comprise functional biomolecules such as enzymes, bacteriocins and antibodies.

Other optional ingredients that may be included are e.g. bleaching agents such as peroxy compounds e.g. sodium percarbonate, potassium peroxydiphosphate, effervescing systems such as sodium bicarbonate/citric acid systems, colour change systems, anti-bad breath ingredients and so on.

Buffers and salts to buffer the pH and ionic strength of the compositions may also be included.

The benefits of the present invention are manifold; the self-heating effect alleviates the pain that people suffering from sensitive teeth normally experience when brushing their teeth with ordinary toothpaste, and this alleviation can even be improved by inclusion of an antisensitive teeth ingredient in the dentifrice such as potassium nitrate.

Furthermore, the self-heating effect can improve the delivery of therapeutically beneficial ingredients, present in the dentifrice such as antimicrobial agents like Triclosan and anti-caries agents such as sodium monofluorophosphate.

The dentifrice of the present invention also provides for an improved cleaning and whitening effect, and reduces bad breath.

The present invention will further be illustrated by the following examples.

EXAMPLE 1

The following formulation is a dentifrice according to the invention.

|  | % by weight |
| --- | --- |
| abrasive silica | 10 |
| thickening silica | 12 |
| sodium carbonate (anhydrous) | 6 |
| propyleneglycol | 61.38 |
| sodium saccharinate | 0.2 |
| monosodium phosphate (anhydrous) | 5 |
| titanium dioxide | 1 |
| sodium fluoride | 0.32 |
| sodium laurylsulphate | 1.8 |
| polyethyleneglycol (MW 1500) | 1 |
| Triclosan | 0.3 |
| flavour | 1 |
| pH (100%): 10.7 | |

EXAMPLE 2

The following formulation is another dentifrice according to the invention.

|  | % by weight |
| --- | --- |
| abrasive silica | 5 |
| thickening silica | 5 |
| sodium carbonate (anhydrous) | 6 |
| polyethyleneglycol (MW 400) | 72.28 |
| sodium saccharinate | 0.3 |
| monosodium phosphate (anhydrous) | 5 |
| titanium dioxide | 1 |
| sodium fluoride | 0.32 |
| sodium laurylsulphate | 1.8 |
| polyethyleneglycol (MW 1500) | 2 |
| Triclosan | 0.3 |
| flavour | 1 |
| pH (100%): 9.36 | |

EXAMPLE 3

The following formulation is yet another dentifrice according to the invention, particularly for sensitive teeth

|  | % by weight |
| --- | --- |
| abrasive silica | 10 |
| sodium carbonate (anhydrous) | 10 |
| propyleneglycol | 34.23 |
| glycerol (water-free) | 10 |
| xanthan gum | 0.1 |
| sodium saccharinate | 0.25 |
| potassium nitrate | 5 |
| monosodium phosphate (anhydrous) | 10 |
| titanium dioxide | 1 |
| sodium fluoride | 0.32 |
| sodium laurylsulphate | 1.8 |
| polyethyleneglycol (MW 1500) | 8 |

EXAMPLES 4 and 5

The following formulations 4 and 5 are also dentifrices according to the present invention:

|  | % by weight No. 4 | % by weight No. 5 |
| --- | --- | --- |
| abrasive silica | 10 | 10 |
| thickening silica | 9 | 8.5 |
| glycerol | 7.5 | 10 |
| xanthan gum | 0.076 | 0.1 |
| titanium dioxide | 1 | 1 |
| sodium carbonate (anhydr.) | 10 | 10 |

-continued

|  | % by weight No. 4 | % by weight No. 5 |
| --- | --- | --- |
| polyethyleneglycol (MW 1500) | 6 | 6 |
| propyleneglycol | 42.254 | 35.23 |
| sodium fluoride | 0.32 | 0.32 |
| sodium laurylsulphate | 1.8 | 1.8 |
| monosodiumphosphate (anhydr.) | 10.5 | 10.5 |
| potassium nitrate | — | 5.0 |
| flavour | 1 | 1 |
| Triclosan | 0.3 | 0.3 |
| pH (100%) | 10.11 | 10.03 |

EXAMPLE 6

The increase in temperature over two minutes was measured of 1:2 slurries (toothpaste/water) of the formulations of Example 1, 4 and 5. For comparison purposes a conventional toothpaste, containing a potassium salt as desensitising agent was also tested as regards a possible temperature increase. The following results were obtained:

| | Temp. (in °C.) | | | Comparison | Example 1 of |
| --- | --- | --- | --- | --- | --- |
| Time (sec) | Ex. 1 | Ex. 4 | Ex. 5 | formulation | US-A-4132771 |
| 0 | 25 | 24 | 24 | 24 | 26 |
| 30 | 30 | 30 | 27 | 24 | 33 |
| 60 | 30 | 30 | 29 | 25 | 33 |
| 90 | 30 | 31 | 29 | 25 | 33 |
| 120 | 30 | 31 | 29 | 25 | 33 |
| Δt (after 120) | 5 | 7 | 5 | 1 | 7 |

Example 1 of U.S. Pat. No. 4,132,771 contained 30% zeolite, and comparing it with Example 4 of the present invention shows, that the same Δt is obtained with a significantly lower level of the hydratable salts of the invention (20.5%).

EXAMPLE 7

The following formulation was prepared:

|  | % by weight |
| --- | --- |
| abrasive silica | 10 |
| thickening silica | 15 |
| propyleneglycol | 59.38 |
| sodium carbonate (anhydr.) | 6 |
| sodium saccharinate | 0.2 |
| monosodium phosphate (anhydr.) | 5 |
| titanium dioxide | 1 |
| sodium fluoride | 0.32 |
| sodium laurylsulphate | 1.8 |
| flavour | 1 |
| Triclosan | 0.3 |
| pH (100%) 9.71 | |

This formulation was tested as to its chemical cleaning ability to remove extrinsic stains, using the following method:

(1) Synthetic hydroxyapatite discs were polished and placed in sterile saliva at 37° C. overnight to form a pellicle.

(2) Discs were stained with tea/coffee/iron salts/saliva mixture for seven days at 37° C.

(3) Stained discs were immersed in slurries of the formulation (1:2 toothpaste/water) for desired time.

(4) The change in colour of the discs was measured using a Minolta chromameter CR-300 in L*a*b mode. Using L* (treated), L* (soiled), and L* (clean), the percentage of stain removed was calculated using the following formula:

$$\text{stain removed} = \frac{L^*(\text{treated}) - L^*(\text{soiled})}{L^*(\text{clean}) - L^*(\text{soiled})} \times 100\%$$

where

L* (soiled)=L* reading of stained disc

L* (clean)=L* reading of pellicle coated disc prior to staining

L* (treated)=L* after treatment with the formulation.

For comparison purposes, the following formulation was also tested:

|  | % by weight |
| --- | --- |
| abrasive silica | 10 |
| thickening silica | 9 |
| cellulose gum | 1 |
| sorbitol (70%) | 45 |
| trisodiumorthophosphate | 0.03 |
| polyethyleneglycol (MW1500) | 5 |
| sodium saccharin | 0.2 |
| titanium dioxide | 1 |
| sodium laurylsulphate | 1.5 |
| flavour | 1.2 |
| water | to 100 |
| pH 6.38 | |

The following results were obtained:

| | Stain removal (in %) | | | |
| --- | --- | --- | --- | --- |
| | after 1 min. | 3 min. | 5 min. | 10 min. |
| control | −2.32 | −3.72 | −2.97 | −3.65 |
| (SD) | (3.90) | (1.75) | (1.57) | (2.49) |
| formulation | 12.14 | 14.71 | 17.75 | 18.55 |
| (SD) | (5.67) | (5.62) | (5.62) | (5.67) |

(SD = Standard Deviation)

EXAMPLE 8

The following formulations showed the following temperature-increase profiles:

|  | % by weight | |
| --- | --- | --- |
|  | (a) | (b) |
| glycerol | 73.59 | 78.59 |
| polyethyleneglycol-600 | 3 | 3 |
| benzoic acid | 0.15 | 0.15 |
| sodium monofluorophosphate | 0.76 | 0.76 |
| silica aerogel | 5 | 5 |
| sodium carbonate (anhydrous) | 15 | 10 |
| sodium laurylsulphate | 1.5 | 1.5 |
| flavour | 1 | 1 |

| | Temp. (in °C.) | |
| --- | --- | --- |
| Time (sec) | (a) | (b) |
| 0 | 25 | 26 |
| 30 | 31 | 30 |
| 60 | 31 | 30 |
| 90 | 31 | 30 |

| | | |
|---|---|---|
| 120 | 31 | 30 |
| Δt | 6 | 4 |

These examples show, in comparison with Example 1 of U.S. Pat. No. 4,132,771, that with substantially lower levels of anhydrous sodium carbonate similar temperature increase profiles are obtained as with 30% anhydrous zeolite.

EXAMPLE 9

Repeating Example 1, but replacing the anhydrous sodium carbonate and/or the anhydrous monosodium phosphate by an equivalent amount of an alkalimetal pyrophosphate, or alkalimetal borate, or alkalimetal sesquicarbonate, or calcium- or magnesiumchloride, or calcium sulphate, or an alkalimetal acetate, or an alkalimetal citrate, or zinc citrate or zinc sulphate or zinc nitrate produces similar temperature-increase effects.

EXAMPLE 10

The following formulation was tested as to its fluoride delivery, in comparison to a standard formulation:

| | % by weight | |
|---|---|---|
| | (A) | Comparison formulation (B) |
| abrasive silica | 4 | 10 |
| thickening silica | 7 | 9 |
| propyleneglycol | 33.38 | — |
| polyethyleneglycol (MW 1500) | 14 | 5 |
| anhydrous sodium carbonate | 15 | — |
| sodium saccharinate | 0.2 | 0.2 |
| titanium dioxide | 1 | 1 |
| sodium fluoride | 0.32 | 0.32 |
| sodium laurylsulphate | 1.8 | 1.5 |
| potassium nitrate | 5 | — |
| monosodium orthophosphate | 17 | — |
| Triclosan | 0.3 | — |
| flavour | 1 | 1.2 |
| water | — | 25.75 |
| sorbitol | — | 45 |
| trisodium phosphate | — | 0.03 |
| cellulose gum | — | 1 |

10 hydroxyapatite disks (4 mm thick) were used for each sample. Each face of the disk was brushed for 1 minute with 1 g of the formulation. Between each treatment the brushed disk was rinsed with demineralized water for 10 seconds and then dipped in dilute hydrochloric acid (0.1M) solution and this acid solution was then analyzed by gaschromatography to determine its fluoride content. The following results after the indicated time periods were obtained:

| Time (hrs) | (A) | ppm fluoride | (B) |
|---|---|---|---|
| 0 | 0.4 | | 0.242 |
| 3 | 0.453 | | 0.244 |
| 7 | 0.456 | | 0.28 |
| 27 | 0.488 | | 0.282 |

We claim:

1. An anhydrous, self-heating dentifrice substantially free from anhydrous synthetic zeolites comprising from 10.5 to 25% by weight of a heat of hydration generating, hydratable inorganic and/or organic salt selected from the group consisting of alkalimetal orthophosphates, alkalimetal pyrophosphates, alkalimetal carbonates, alkalimetal sesquicarbonates, alkalimetal borates, calcium chloride, magnesium chloride, calcium sulphate, alkalimetal acetates, alkalimetal citrates, alkalimetal phosphonates, zinc citrate, zinc sulphate, zinc nitrate and mixtures thereof.

2. A dentifrice according to claim 1, wherein the hydratable salt is present in an amount of from 15 to 20% by weight of the dentifrice.

3. A dentifrice according to claim 1, wherein the hydratable salt is an anhydrous salt.

4. A dentifrice according to claim 1, wherein the salt is anhydrous sodium carbonate.

5. A dentifrice according to claim 1, wherein upon brushing teeth within an oral cavity, temperature of a combination of the dentifrice with a saliva mixture increases over an initial temperature by an amount from 3° to 15° C. after 2 minutes of brushing.

* * * * *